United States Patent
Sali et al.

(10) Patent No.: US 7,916,286 B2
(45) Date of Patent: *Mar. 29, 2011

(54) DEFECT DETECTION THROUGH IMAGE COMPARISON USING RELATIVE MEASURES

(75) Inventors: Erez Sali, Savion (IL); Oren Cohen, Holon (IL)

(73) Assignee: Applied Materials South East Asia Pte. Ltd., Singapore (SG)

(*) Notice: Subject to any disclaimer, the term of this patent is extended or adjusted under 35 U.S.C. 154(b) by 630 days.

This patent is subject to a terminal disclaimer.

(21) Appl. No.: 11/958,731

(22) Filed: Dec. 18, 2007

(65) Prior Publication Data

US 2008/0101686 A1    May 1, 2008

Related U.S. Application Data

(63) Continuation of application No. 11/590,650, filed on Oct. 31, 2006, now Pat. No. 7,369,236.

(51) Int. Cl.
  *G01B 11/00* (2006.01)
  *G01N 21/00* (2006.01)
  *G06K 9/00* (2006.01)
  *G06K 9/03* (2006.01)

(52) U.S. Cl. .............. 356/237.1; 356/237.4; 356/237.5; 356/394; 382/149; 382/154

(58) Field of Classification Search .............. 356/394, 356/237.1–237.5; 382/8, 25, 30, 144–145, 382/149, 154
See application file for complete search history.

(56) References Cited

U.S. PATENT DOCUMENTS

| | | | |
|---|---|---|---|
| 4,579,455 A | 4/1986 | Levy et al. | |
| 4,791,586 A * | 12/1988 | Maeda et al. | 716/5 |
| 4,809,341 A | 2/1989 | Matsui et al. | |
| 4,845,558 A * | 7/1989 | Tsai et al. | 348/126 |
| 5,146,509 A | 9/1992 | Hara et al. | |
| 5,574,800 A * | 11/1996 | Inoue et al. | 382/149 |
| 5,619,588 A * | 4/1997 | Yolles et al. | 382/149 |
| 5,767,974 A | 6/1998 | Higashiguchi et al. | |
| 5,850,467 A | 12/1998 | Matsui et al. | |
| 5,943,437 A | 8/1999 | Sumie et al. | |
| 6,072,897 A | 6/2000 | Greenberg et al. | |
| 6,141,038 A * | 10/2000 | Young et al. | 348/87 |
| 6,148,114 A * | 11/2000 | Han | 382/256 |
| 6,222,935 B1 * | 4/2001 | Okamoto | 382/149 |
| 6,466,314 B1 | 10/2002 | Lehamn | |

(Continued)

OTHER PUBLICATIONS

"Golden Template Comparison", William A. Silver, Sensors Magazine, Oct. 1990, vol. 7, No. 11, pp. 20-26.

(Continued)

*Primary Examiner* — Sang Nguyen
(74) *Attorney, Agent, or Firm* — SNR Denton US LLP

(57) ABSTRACT

Inspection of objects such as semiconductor wafers can include comparisons of shapes between inspection and reference images. As part of the inspection process, relative values may be assigned to pixels within each image based on comparison of such pixels to neighboring pixels. For instance, the pixels may be ranked by relative brightness in each image. Alternatively, directional vectors may be defined based on slopes between pixels and their neighbors. Various comparison metrics may be utilized to determine the degree of correlation between the relative values for pixels in the inspection image and corresponding pixels in the reference image. Relative values may be combined with conventional techniques as part of an inspection process. The inspection may be performed using an optical inspection tool that uses conventional techniques to identify defect candidates, with relative value analysis performed on areas containing defect candidates to confirm or deny the existence of a defect.

20 Claims, 6 Drawing Sheets

U.S. PATENT DOCUMENTS

| | | | |
|---|---|---|---|
| 6,909,798 B1 * | 6/2005 | Yukawa et al. | 382/141 |
| 7,155,052 B2 * | 12/2006 | Geshel et al. | 382/144 |
| 7,369,236 B1 * | 5/2008 | Sali et al. | 356/394 |
| 2004/0146295 A1 | 7/2004 | Furman et al. | |
| 2006/0193506 A1 | 8/2006 | Dorphan et al. | |
| 2006/0193507 A1 * | 8/2006 | Sali et al. | 382/145 |

OTHER PUBLICATIONS

"Ordinal Measures for Image Correspondence", Bhat et al., IEEE Transactions on Pattern Analysis and Machine Intelligence, Apr. 1998, vol. 20, No. 4, pp. 415-423.

* cited by examiner

Inspected Image $I_{x,y}$

| 10 | 20 | 30 |
|----|----|----|
| 50 | 40 | 70 |
| 60 | 90 | 80 |

| 1 | 2 | 3 |
|---|---|---|
| 5 | 4 | 7 |
| 6 | 9 | 8 |

$\text{Ord}[I_{x,y}] = I^{ord}_{x,y}$

Reference Image $R_{x,y}$

| 90 | 60 | 70 |
|----|----|----|
| 50 | 40 | 80 |
| 10 | 30 | 20 |

| 9 | 6 | 7 |
|---|---|---|
| 5 | 4 | 8 |
| 1 | 3 | 2 |

$\text{Ord}[R_{x,y}] = R^{ord}_{x,y}$

DEFECT DETECTION THROUGH IMAGE COMPARISON USING RELATIVE MEASURES

RELATED APPLICATIONS

The present application is a continuation application of U.S. patent application Ser. No. 11/590,650 filed Oct. 31, 2006, which is incorporated by reference in its entirety herein.

BACKGROUND

In the semiconductor industry, devices are fabricated by a number of processes to produce precisely-defined structures of an ever-decreasing size. Even the slightest structural defect can ruin a semiconductor device, and so to avoid losses of time and effort, detection of defects is critical before a defective device is mass-produced or further processes are performed on a defective wafer. Various inspection tools may be utilized, including those in which a view of a wafer (or other device or object) is compared to a reference image showing the wafer in a defect-free state. A reference image or images may be used, such as views of portions of the same wafer that (ideally speaking) contain the same structural features, for example.

Many optical inspection tools perform defect detection based on comparing gray levels between images. For instance, an inspection image $I_{x,y}$ may be obtained for comparison to a reference image $R_{x,y}$. Defects may be detected by subtracting the images ($I_{x,y}-R_{x,y}$) and using various algorithms to determine the existence (or non-existence) of defects by evaluating the subtraction image. See, for example, U.S. patent application Ser. No. 10/345,097, filed Jun. 15, 2003, which is hereby incorporated by reference for all purposes herein.

Other comparison formulas have been discussed in varying degrees of detail. For instance, in "Golden Template Comparison" by William A. Silver (Sensors, Oct. 1990), the use of a correction function on the inspection image, along with another function performed on the subtraction image is discussed. U.S. Pat. No. 4,579,455 discusses an inspection system that includes summing neighboring pixels to aid in determining the presence or absence of a defect.

However, there is a need for improvement in various applications to improve the detection of defects while also avoiding or eliminating false alarms. For instance, using dark-field imaging on patterned dies may lead to false alarms when gray level comparisons are used alone. For example, differences in the slopes of edges, wafer layer widths, and/or slight defocusing of the image may cause significant differences between reference and inspection image gray levels even though no defect is present.

SUMMARY

Methods of inspecting an object such as a semiconductor wafer can include determining the similarity of pattern shapes between an inspection image and a reference image. Shapes may be compared by assigning relative values to pixels in each image based on their neighboring pixels and then comparing relative values in area(s) of the inspection image to relative values in corresponding area(s) of the reference image. Comparing shapes rather than gray levels alone advantageously reduces the false alarm rate. For example, false alarms due to gray level differences in non-defective areas caused by process variation or change in the image conditions can be reduced since the shape of the area is considered.

A method of detecting defects can include obtaining an inspection image depicting at least a part of an object, such as a semiconductor wafer, reticle, or other object. The image may be obtained using an optical inspection system. The method may further include obtaining a reference image representing the same part of the object shown in the inspection image as said part would appear in a substantially-defectless state. For instance, the reference image may comprise an image of another part of the object or an aggregate of inspection images, for example. The method may further comprise comparing at least a portion of the inspection image to a corresponding portion of the reference image.

Comparing may include determining the degree of similarity between the portion of the inspection image and the portion of the reference image by comparing relative values of one or more pixels in the inspection image to relative values of one or more corresponding pixels in the reference image and flagging the compared portions based on comparing the degree of similarity to a threshold value. If shapes in the areas in the inspection image and reference image are similar, the relative values will also be similar. However, if the shapes are different, the relative values will differ.

For example, the relative values may comprise ordinal ranks of a pixel relative to its neighboring pixels. Determining the degree of similarity can include applying a comparison metric to the ordinal ranks to determine how close ranks in the inspection image are to ranks in the reference image for the same area. The ordinal ranks may be determined by ranking the relative brightness of a pixel as compared to pixels in a neighborhood of varying size. For instance, the pixel's 4-neighborhood, 8-neighborhood, or larger neighborhoods may be used. Neighboring pixels may be adjacent or non-adjacent.

Any suitable comparison metric may be used to compare the ordinal ranks in the inspection image to the ordinal ranks in the reference image. For instance, Regular Distance Metrics and Hamming Distance metrics may be utilized. Metrics based on permutations may be suitable, as well. A permutation-based distance metric may define a permutation of the ranks in the inspection image and a permutation of the ranks in the reference image. The reference permutation may be composed with the inspection permutation to define a composition permutation, which may then be compared to a unity permutation of the same length. The degree of difference between the inspection and reference permutations can be determined based on the distance between the composition permutation and the unity permutation.

Reference images may be obtained in any suitable manner. For example, a plurality of images depicting the same structural elements as shown in the inspection image may be accumulated or otherwise combined to generate a reference image.

Prior to comparing the inspection and reference images through use of relative values, the images may be compared in a preliminary image comparison using any suitable technique(s) to identify one or more defect candidates. The areas including the defect candidates may then be compared using relative measures, which may advantageously reduce computational requirements. For instance, the preliminary image comparison may include a gray level comparison. Alternatively, entire inspection images may be compared to entire reference images using relative measures.

In some embodiments, one or more defects may be detected based on comparing relative values in the inspection image and the reference image. After identification, the defect(s) can be classified, including comparing the assigned relative values for the portion of the image comprising the at least one defect(s) to relative values in one or more defect reference images.

Another exemplary comparison methodology based on relative measures uses directional vectors based on slopes or slants between pixels. When comparing a reference and inspection image, the directional slope between a pixel and its neighbors may first be determined in each image. Then, the directional slopes for the pixel or pixels in the inspection image may be compared to the directional slopes for the corresponding pixel or pixels in the reference image to determine the degree to which the directional slopes match.

Directional slopes between pixels may be determined based on comparing the magnitude of difference in gray level between the pixels and the sign of the difference. The slope may be determined based on a threshold value, with no slope indicated if the magnitude does not meet the threshold. The threshold may be constant, user-specified, or adaptive. For instance, the slope may be defined as increasing, decreasing, or undetermined (i.e. neither increasing nor decreasing). Alternatively, the slope may be defined using more or fewer degrees of description. For instance, to conserve computing resources, the slopes may be defined as increasing or not-increasing, with the latter case including both decreasing and undetermined slopes.

A method of detecting defects can include obtaining an inspection image and a corresponding reference image of an object, such as a semiconductor wafer. At least one suspected defect in the inspection image may be identified through a preliminary image comparison. For each suspected defect, an area surrounding the defect in the inspection image and a corresponding area in the reference image may be selected. For each pixel in each selected area, slope values for the pixel relative to its surrounding pixels may be established. Each pixel may be replaced by a pixel slope correlation value representing the amount of correlation between the reference and inspection images.

The reference image and inspection image may be compared by a gray level comparison. Each pixel of the subtraction image from that comparison may be divided by a factor, with the resulting image added to the pixel slope correlation image to obtain a total comparison image. A sum operator may be applied to the total comparison image. The average of the five highest values in the area after the sum operator has been applied may be compared to determine if the average exceeds a threshold value. For example, the area may be indicated as containing a defect, or may be highlighted for further analysis and/or processing if the threshold is exceeded.

An electro-optical inspection system can include a light source configured to illuminate an object, an imager operative to obtain an image of the object, and at least one processing unit. The processing unit may be configured to carry out steps including obtaining an inspection image of the object, accessing a reference image depicting the same structural features of the object as they would appear in a substantially-defectless state, assigning relative values to pixels in the inspection image and to corresponding pixels in the reference image, comparing relative values for pixels in the inspection image to relative values for pixels in the reference image, and indicating an area as containing a suspected defect based on the comparison results.

The system may be further configured to combine images depicting like structural features of the object and store the combination as a reference image. Relative values may be assigned by ranking pixels based on relative brightness. Relative values may be assigned by assigning directional slope indicator values based on the direction of the change of brightness between pixels.

BRIEF DESCRIPTION OF THE DRAWINGS

A full and enabling disclosure, including the best mode of practicing the appended claims, directed to one of ordinary skill in the art, is set forth more particularly in the remainder of the specification, which makes reference to the appended figures, in which:

FIG. 3 depicts exemplary portions of an inspection image and a reference image;

FIG. 4 shows exemplary windows which may be used in comparisons of an exemplary image;

Use of like reference numerals in different features is intended to illustrate like or analogous components.

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents.

As noted above, the present subject matter generally pertains to determining the presence or absence of a defect by comparing the shapes depicted in a reference and inspection image. For instance, relative values indicating the relationship(s) between pixels within an inspection image may be compared to relative values of corresponding pixels in a reference image. Based on comparing the relative values, the degree of similarity or dissimilarity in the shapes depicted in the inspection and reference images may be assessed. If shapes are too dissimilar, a defect may be present. Although specific examples of relative values are discussed herein, other relative values may be suitable for use based on the teachings contained herein. Similarly, specific types of inspection tools, modes, and inspection objects are also discussed herein, but for purposes of example only. For instance, the objects inspected may include not only semiconductor wafers, but also other objects of any size, shape, or configuration.

Figure 1:
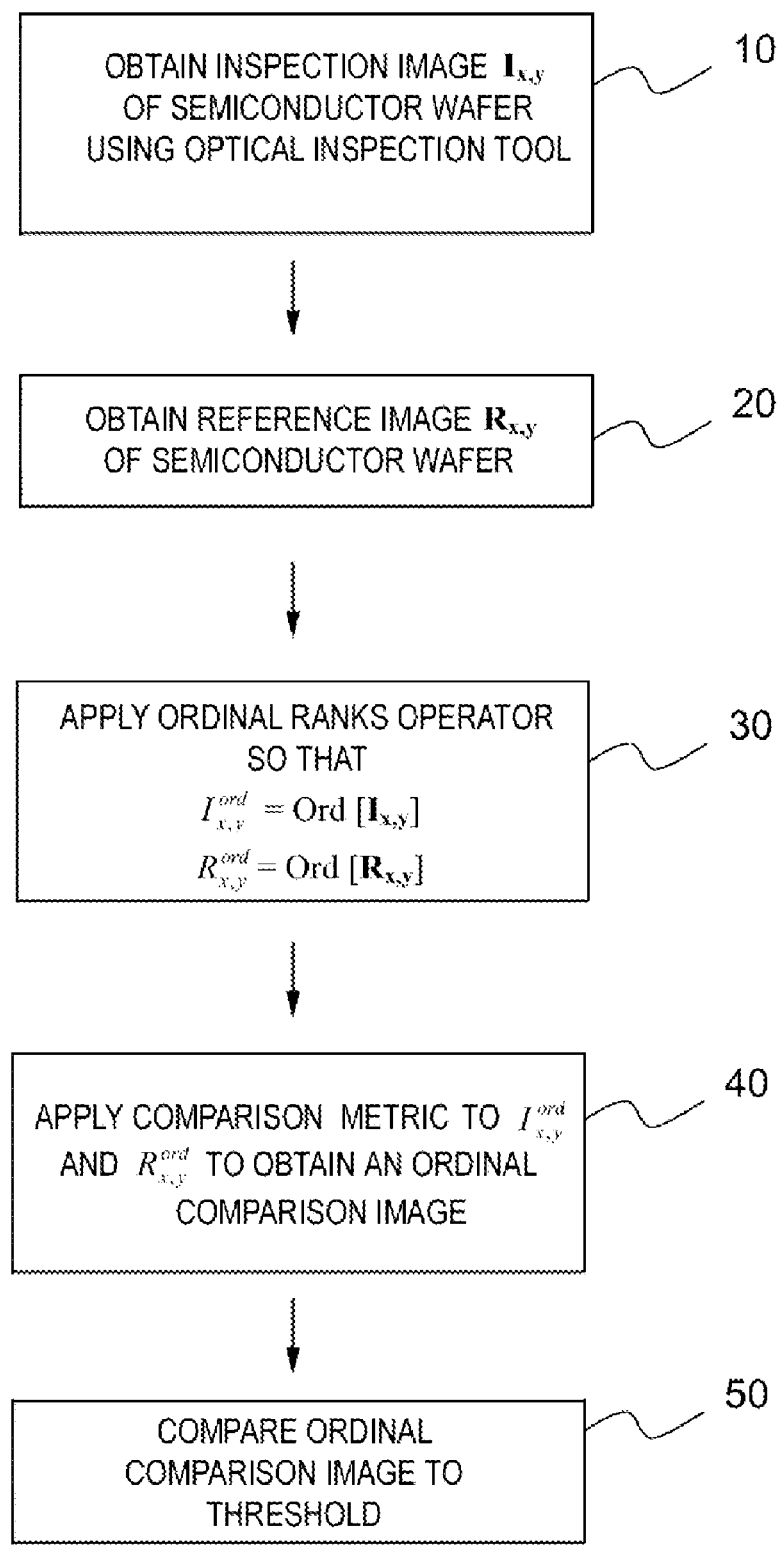
FIG. 1 is a flowchart showing exemplary steps that may be included in a method of detecting defects using ordinal ranks.

FIG. 1 is a flow chart illustrating exemplary steps in an inspection process that includes comparison of relative values between images. At 10, an inspection image $I_{x,y}$ depicting at least a portion of an object may be obtained using an optical inspection tool. In the examples used herein, x and y refer to row and column coordinates, respectively, within an image.

For instance, $I_{3,7}$ refers to the pixel in image I where x=3 and y=7. The discussion herein uses rectangular coordinates and rectangular images for purposes of example only; one of skill in the art will appreciate that other coordinate systems and/or arrangements of pixels may be utilized.

Any suitable tool may be used to obtain one or more inspection images or portions thereof, for example, a Negevtech 302 wafer inspection tool, commercially available from Negevtech Ltd., 12 Hamada Street, Rehovot Israel 76703, operating in bright-field, dark-field, or other illumination mode. At 20, a reference image $R_{x,y}$ is obtained, with the reference image depicting the same structural features shown in the inspection image as such features would appear in a substantially-defectless state.

For example, the reference image may be accessed from a file or memory included in the inspection tool or accessible by the tool. The reference image may be generated by the inspection tool based on combining images depicting portions of an object that are (ideally, at least) identical. For instance, in a semiconductor wafer, images of identical dies may be combined, averaged, or otherwise accumulated during the inspection process to provide a reference image. Alternatively, an image of an adjacent or nearby feature of the object (such as an adjacent die of a semiconductor wafer) may be used. The particular form through which the reference image is obtained is relatively unimportant.

Although not shown in the figure, one of skill in the art will appreciate that, as a preliminary step prior to comparing I and R, the images are preferably aligned using any suitable technique, such as by the nearest neighbor method, bilinear filtering, or same-smear filtering, such as described in U.S. patent application Ser. No. 11/068,711.

At step 30, relative values are applied to at least some of the pixels in the inspection image and at least some of the corresponding pixels in the reference image. In the example of FIG. 1, an operator is used to rank pixels in I and R relative to neighboring pixels. For instance, pixels in neighborhoods of varying sizes may be ranked. Depending upon the particular operator that is used, the ranked pixels may not necessarily be adjacent.

At step 40, a comparison metric is applied to the ordinal ranks in I and R to define an ordinal comparison image. Each pixel location in the ordinal comparison image corresponds to the comparison results for an ordinal comparison between the reference image and the inspection image "centered" on that pixel (although as will be noted below, comparisons do not need to have the pixel in question at the actual center). Then, at step 50, pixels in the ordinal comparison image may be evaluated against one or more thresholds to determine whether or not further action is required. A non threshold-based comparison may be applied as well. For example, a specified number of pixels in the comparison image with the highest values (relative to other pixels in the comparison image) may be noted or flagged.

The particulars of applying the ordinal ranks operator and comparison metric will now be discussed in more detail in conjunction with FIG. 3. FIG. 3 depicts gray levels in an exemplary inspection image $I_{x,y}$ and an exemplary corresponding reference image $R_{x,y}$. This example shows a 3×3 window; however, one of ordinary skill in the art will appreciate that the size and arrangement of sets of pixels may be varied. FIG. 3 also shows the result of applying an ordinal ranking operator to each image. In this example, $I_{x,y}^{ord}$ and $R_{x,y}^{ord}$, represent ordinal rankings of the pixels by gray levels from lowest to highest. However, other ordinal rankings may be used, such as highest to lowest. In some embodiments, pixels with the same or close gray levels may receive the same rank.

The ordinal rankings may be determined by any suitable algorithm. For example, the rankings may be determined using a threshold that may be predetermined or adaptive based on the gray levels within the window or throughout the image. The rankings may be linear or non-linear. Furthermore, the rankings may be based upon the gray levels alone or may be determined after one or more operations have been performed, such as filtering or smoothing. Rankings may be based on factors other than gray levels, as well.

Once ordinal ranks have been obtained for I and R, the shapes of the images may be compared by comparing the ordinal ranks. As is the case with obtaining ordinal ranks, comparison of ordinal ranks may be performed using hardware, software, or any suitable combination thereof. For instance, Regular Distance Metrics of the form $$\sum_{x,y} |I_{x,y}^{ord} - R_{x,y}^{ord}| \text{ or} \tag{Eq. 1}$$

$$\sum_{x,y} (I_{x,y}^{ord} - R_{x,y}^{ord})^2 \tag{Eq. 2}$$

may be suitable. Using Equation (1) and the exemplary images in FIG. 3, the distance between the ordinal ranks of $I^1_{x,y}$ and $R^1_{x,y}$ is 34.

Hamming Distance Metrics may also be suitable, generally following the form $$\sum_{x,y} \text{Sign}|(I_{x,y}^{ord} - R_{x,y}^{ord})|, \text{Sign}(\alpha) = \begin{cases} 1 & \alpha > 0 \\ 0 & \alpha = 0 \\ -1 & \alpha < 0 \end{cases} \tag{Eq. 3}$$

Equation (3) gives a distance of 7 between the ranks for $I_{x,y}$ and $R_{x,y}$.

A permutation-based distance measure may also be suitable for comparing ordinal ranks. Permutation based distance measurements are explained in more detail in "Ordinal Measures for Image Correspondence" by Dinkar N. Bhat and Shree K. Nayaer in IEEE Transactions on Pattern Analysis and Machine Intelligence, April 1998 (Vol. 20, No. 4).

The rank data for $I_{x,y}$ and $R_{x,y}$ may be considered as two permutations, $\Pi_{inspected}$ and $\Pi_{reference}$. For the example of FIG. 3, the rank permutations are:

$$\Pi_{inspected} = \{1,2,3,5,4,7,6,9,8\} \tag{Eq. 4); and}$$

$$\Pi_{reference} = \{9,6,7,5,4,8,1,3,2\} \tag{Eq. 5).}$$

A composition permutation, S, is defined by composing $\Pi_{reference}$ and the inverse permutation of $\Pi_{inspected}$. For the above examples, S={9,6,7,4,5,1,8,2,3} (Eq. 6). For a perfect match between $\Pi_{inspected}$ and $\Pi_{reference}$, S is the unity permutation ($S_{perfect\ match}$) having the same length as $\Pi_{inspected}$ and $\Pi_{reference}$. In this example:

$$S_{perfect\ match} = \{1,2,3,4,5,6,7,8,9\} \tag{Eq. 7).}$$

By finding the distance between S and Sperfect match, the degree of variation between the permutations (and thus the degree of difference in shape between the images) may be measured.

Various suitable distance measures may be used to determine the distance. For instance, the Dinkar article noted above includes a distance measure in its discussions of permutations. However, a more simplified distance measure may be suitable for use in the optical inspection context in order to conserve computational resources by reducing the intensity and number of operations which are performed. For example, a distance measure $D_m$ may be defined as follows $$D_m^i = i - \sum_{j=1}^{i} Ind(S^j \le i) = \sum_{j=1}^{i} Ind(S^j > i) \quad \text{(Eq. 8)}$$

$$Ind(x) = \begin{cases} 0 & x \text{ is false} \\ 1 & x \text{ is true} \end{cases}.$$

Using equation 8, the distance measure between the inspection and reference permutations is:

$$D_m = \{1,2,3,3,3,2,2,1,0\} \quad \text{(Eq. 9)}.$$

The comparison result for 1 and R may be derived from the maximal value of Dm, for example, using Eq. 10:

$$\kappa = 1 - \frac{2\max(D_m)}{\lceil n/2 \rceil}. \quad \text{(Eq. 10)}$$

In the example of FIG. 3, $\kappa = -0.5$, which indicates a relatively large change between the images. Other results may be obtained based on $D_m$ and used for determining the presence or absence of defects. For instance, the average value of $D_m$ may be calculated.

The above examples discussed the use of ordinal measures and distance metrics generally with regard to an exemplary 3×3 pixel window. One of skill in the art will recognize that there are a wide variety of available options in defining windows for the purposes of optical inspection. Furthermore, it will be apparent that the window does not need to be rectangular or symmetric. It will be still further apparent that the window need not have a particular predetermined shape and may have any number of pixels. The methods and systems disclosed herein may utilize pixels that are connected, not connected, or may utilize combinations of connected and not-connected pixels.

Figures 4A, 4B, 4C:
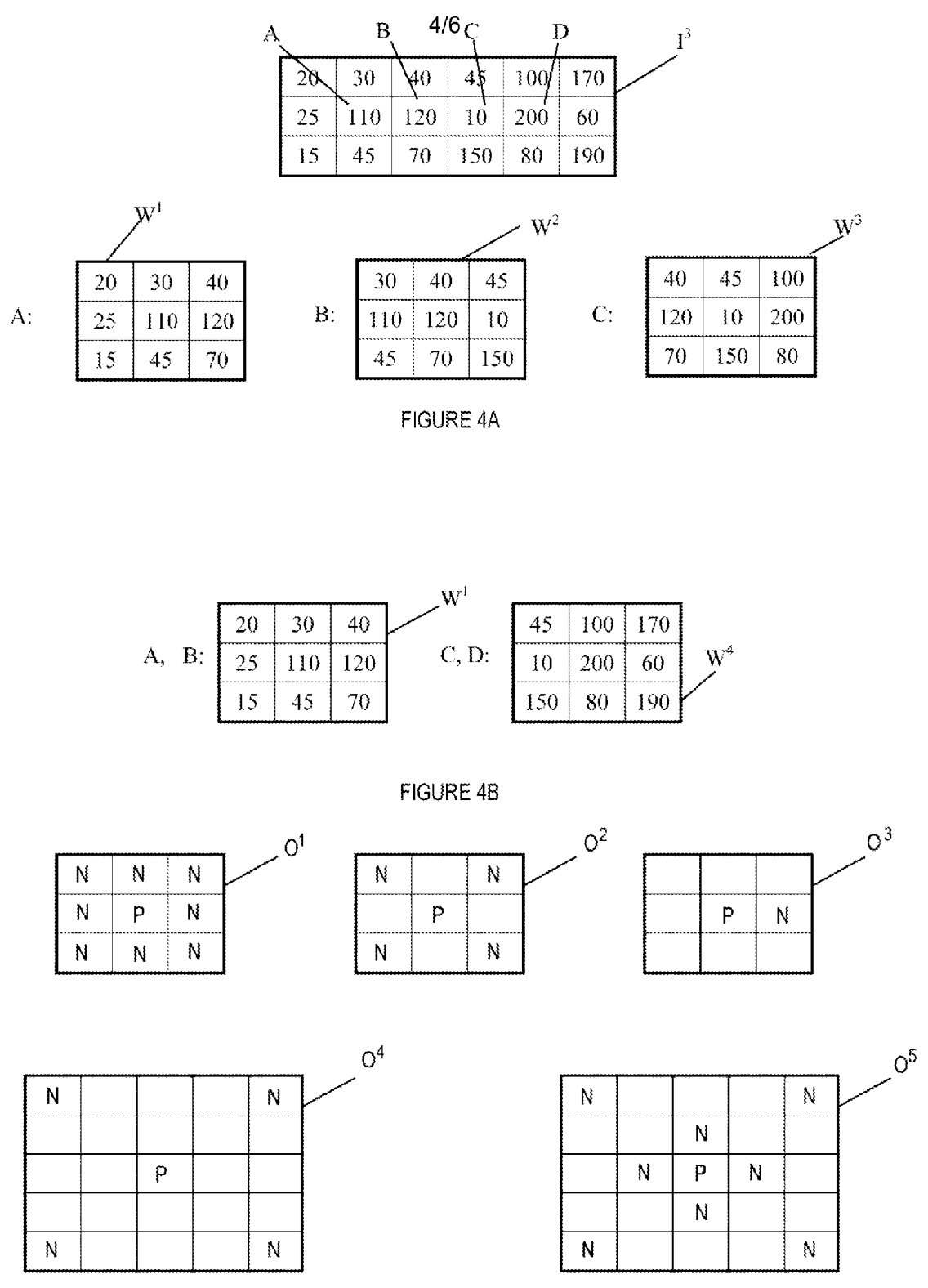

FIGS. 4A 4B, and 4C illustrate examples of how various windows may be defined. In FIG. 4A, an image $I^3$ is a 3×6 array of pixels. Included in $I^3$ are pixels A, B, C, and D. FIG. 4A illustrates three exemplary windows $W^1$, $W^2$, and $W^3$ which may be utilized in an embodiment of object inspection in which a running window operator is used. $W^1$ is centered on pixel A, $W^2$ is centered on pixel B, and $W^3$ is centered on pixel C. For each window, ordinal ranks in $I^3$ and a corresponding reference image may be applied, and one or more distance metrics may be used to determine the degree of similarity between $I^3$ and its reference image.

However, one of ordinary skill in the art will appreciate that use of a running-window operator may be computationally intense. Accordingly, a jumping-window operator may be used. As shown in 4B, only two windows ($W^1$ and $W^4$) are defined, but all of pixels A, B, C, and D are included.

Window operators may additionally or alternatively comprise different shapes. For example, FIG. 4C depicts five different exemplary window operators which may be used in various alternative embodiments of the present subject matter. In these examples, "P" represents the pixel under consideration (i.e. the "center" of the window, although the pixel under consideration need not be in the center of the window) while "N" represents the neighboring pixels used to determine ordinal ranks, directional slopes, or other relative indicators of intensity. For example, $O^1$ uses the 8-neighborhood of P, $O^2$ uses the 4-neighborhood of P, and $O^3$ uses a single neighbor. $O^4$ and $O^5$ depict examples of the use of neighboring pixels that are not all adjacent to P. One of skill in the art will recognize that further variation, alteration, and selection of pixels for use in window operators is entirely within the spirit and scope of the present subject matter. For instance, other variations could include, but are not limited to, changing the number of neighboring pixels beyond what is shown in these examples and/or using combinations of some adjacent and some non-adjacent pixels.

The type and size of windows that are used in the inspection process may be varied by one of ordinary skill in the art based on balancing factors such as cost, speed, performance, and accuracy. The accuracy and speed is a complex function of the algorithm, window size, and window method (i.e. jumping versus running). For instance, generally speaking, using running windows results in heavier computation but more accurate results than using jumping windows.

As a further alternative, the operator may be calculated only once using the data in the entire image area that is under consideration. While this method may sacrifice a certain degree of accuracy, it may be advantageous in that it is also relatively faster than both running and jumping windows.

Figure 2:
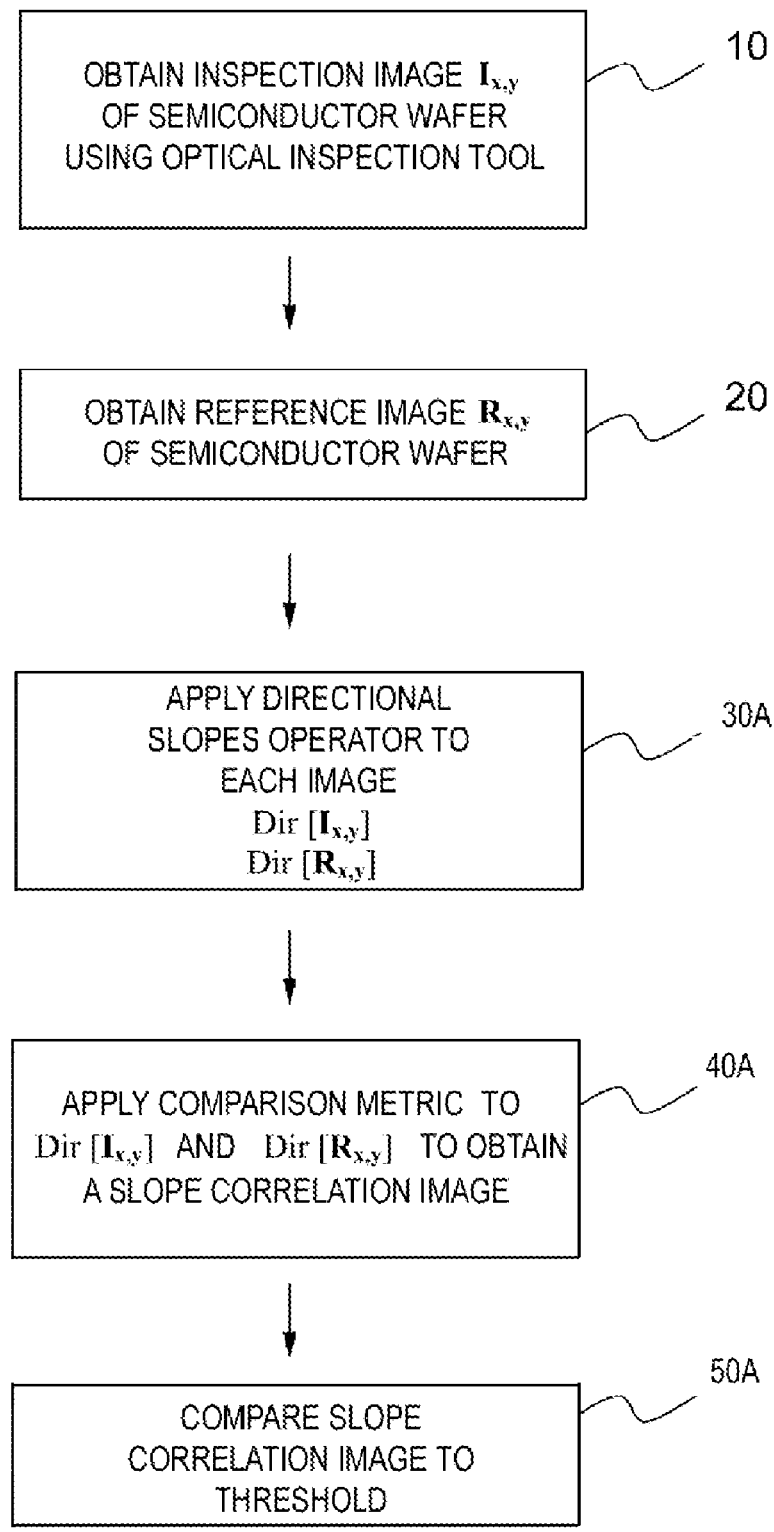
FIG. 2 is a flowchart showing exemplary steps that may be included in a method of detecting defects using slope comparisons.

As noted above, other types of relative values may be used as the comparison basis. FIG. 2 is a flowchart depicting exemplary steps in an alternative inspection process that includes comparison of another type of relative values between images. In the example of FIG. 2, the relative values are directional vectors (i.e. slopes or slants) between pixels. After obtaining an inspection and reference image at steps 10 and 20, at step 30A a directional slope operator is applied to pixels in $I_{x,y}$ and $R_{x,y}$. At step 40A, the comparison metric is used to determine the degree of similarity between directional slopes and create a slope correlation image. At step 50A, the pixels in the slope correlation image may be compared to one or more thresholds, for example, to identify defects or areas for further consideration. Of course, non-threshold-based identification could be used, as well.

The directional vectors may be defined by comparing gray levels of each pixel to one or more of its neighbors. For instance, in one embodiment, each pixel is compared to each of its 8-neighbors. In alternative embodiments, more or fewer neighbors may be compared. For example, comparing a pixel to its 4-neighbors may be less computationally intense. Returning to FIG. 3, the exemplary images $I^1_{x,y}$ and $R^1_{x,y}$ will be again considered, this time in the context of determining directional vectors. Various window shapes, types, and configurations may be used in the comparison of directional slopes, including any of the windows or variants thereof discussed above in conjunction with FIGS. 4A, 4B, and 4C.

A directional vector operator may be applied to 11 and $R^1$ to determine the slopes between pixels within each image. For this example, slopes of the 8-neighbors of the pixel located at x=2, y=2 in each image (i.e. $I^1_{2,2}$ and $R^1_{2,2}$) will be discussed. The directional vector operator may define various relationships between the pixels.

In this example, the vector will be described as undetermined if the magnitude of the difference between gray levels does not exceed a given threshold (in this example, the magnitude of the difference must exceed 10 gray levels). For differences that exceed the threshold, the vector will be described as increasing if the gray level of the neighbor of the pixel in question is less the gray level of the pixel in question. The vector will be described as decreasing if the neighbor has a higher gray level. After directional vectors have been defined, the vectors may be compared. An exemplary comparison ruleset is set forth below.

TABLE 1

Exemplary Rules for Comparison Between I and R

| Inspected | Reference | Comparison |
|---|---|---|
| Increasing | Increasing | 0 |
| Increasing | Undetermined | 0 |
| Increasing | Decreasing | 1 |
| Undetermined | Increasing | 0 |
| Undetermined | Undetermined | 0 |
| Undetermined | Decreasing | 0 |
| Decreasing | Increasing | 1 |
| Decreasing | Undetermined | 0 |
| Decreasing | Decreasing | 0 |

Using the exemplary rules in set forth above, determining directional vectors for $I^1_{2,2}$ and $R^1_{2,2}$ yields the following vectors and comparison results.

TABLE 2

Exemplary Comparison Results

| Direction | Inspected | Reference | Comparison |
|---|---|---|---|
| ↑N | Increasing | Decreasing | 1 |
| ↗NE | Undetermined | Decreasing | 0 |
| →E | Decreasing | Decreasing | 0 |
| ↘SE | Decreasing | Increasing | 1 |
| ↓S | Decreasing | Undetermined | 0 |
| ↙SW | Decreasing | Increasing | 1 |
| ←W | Undetermined | Undetermined | 0 |
| ↖NW | Increasing | Decreasing | 1 |

Under the exemplary rules used here, a perfect match would result in a total comparison sum of 0, while a complete mis-match results in a total comparison sum of 8. Here, the comparison sum result for pixel (2,2) is 4, since the comparison is different for N, NW, SE, and SW.

This value may be used to generate a slope correlation image $C_{x,y}$, where each pixel (x,y) in C corresponds to the comparison sum result based on comparing the directional vectors for the pixel (x,y) in I and R. For example, $C_{2,2}=4$.

One of skill in the art will appreciate that the rules for defining the directional vectors as well as the comparison results may be varied in order to fine-tune the inspection process. For instance, directional vectors may be defined for more or fewer neighbors, such as only considering pixels in the N, S, E, and W directions, or by including both the immediate neighbors of a pixel along with further neighbors.

Furthermore, it is possible to use more or fewer characterizations of the directional vectors. For example, vectors may be defined as "increasing" and "not-increasing" only, where "not-increasing" would include both decreasing and undetermined cases. As a further example, the degree of the increase or decrease may be indicated, such as defining vectors as "increasing," "strongly increasing," "decreasing," "strongly decreasing," "undetermined," etc.

Still further variations may be obtained through defining the threshold and calculations used to characterize the vectors. For instance, the threshold may be preset or adaptive based on the gray levels in the particular image for which directional vectors are being assigned.

As discussed above, use of relative values such as ordinal ranks or directional vectors may allow for more accurate image comparison results in an optical inspection tool. For example, an inspection image and a reference image may be compared to one another on a pixel-by-pixel basis using relative values and, based on the comparison results, a defect may be indicated.

Methods and systems for optical inspection may utilize relative values for a portion of the inspection process in combination with more conventional comparisons. For example, a comparison such as |I−R| may be performed to obtain a difference image which is then scaled by a factor. A comparison based on relative values, such as using ordinal ranks or directional vectors may be performed on the original images and the relative-value-based output scaled by a second factor. The total comparison may be the sum of the scaled difference image and the scaled relative-value-based output image.

In certain contexts, the increased accuracy from using relative-value-based comparisons comes at the cost of heavy computations, which could result in a slower and/or more expensive inspection tool. Therefore, the comparisons using relative values may be utilized as part of an inspection process that uses less computationally-intense methods to first identify suspect areas.

For example, an inspection tool may identify areas of an image that contain defect candidates based on I−R. U.S. patent application Ser. No. 11/069,712, filed Feb. 25, 2005, which is hereby incorporated by reference herein in its entirety, discusses identifying areas containing suspected defects based on calculations including a comparison of gray levels in I to gray levels in R. Such a method could be used to identify defect candidates, and the area or areas in the image containing defect candidates could be subjected to analysis using relative values. Such analysis could be skipped for areas that do not contain suspected defects.

Alternatively, areas without suspected defects could be subjected to analysis using relative values, but such analysis could be a less-intense version of that used on areas with defect candidates. For example, in a system using directional vectors, the areas containing defect candidates could be subjected to analysis using increasing, decreasing, and undefined vectors based on 8 neighbors, while areas without defect candidates could be subjected to analysis using increasing and not-increasing vectors based on only 4 neighboring pixels.

Relative values, whether ordinal ranks, directional slopes, or another type, may also be used in further operations in an inspection system. One exemplary operation uses comparisons of ordinal ranks to sort or classify detected defects. For instance, an inspection tool could identify one or more defects using any suitable detection methodology or combinations thereof, including gray level comparisons and/or relative values. Then, pixels in areas of images containing the defects that have been identified could be assigned relative values. If the defect detection process utilizes relative values, of course, the previously-calculated relative values could be used. The relative values for the defect images could then be compared to relative values for one or more defect reference images in order to identify the type of defect(s) that have been detected. The defect reference images may be processed using relative values in the same manner for the other reference images as set forth above. Alternatively, however, if the same defect reference images are used for multiple comparisons, the defect images may be pre-processed and maintained as sets of relative values for ready comparison. One of skill in the art will recognize that pre-processed relative values may be used for the other reference images above, as well.

Figure 5:
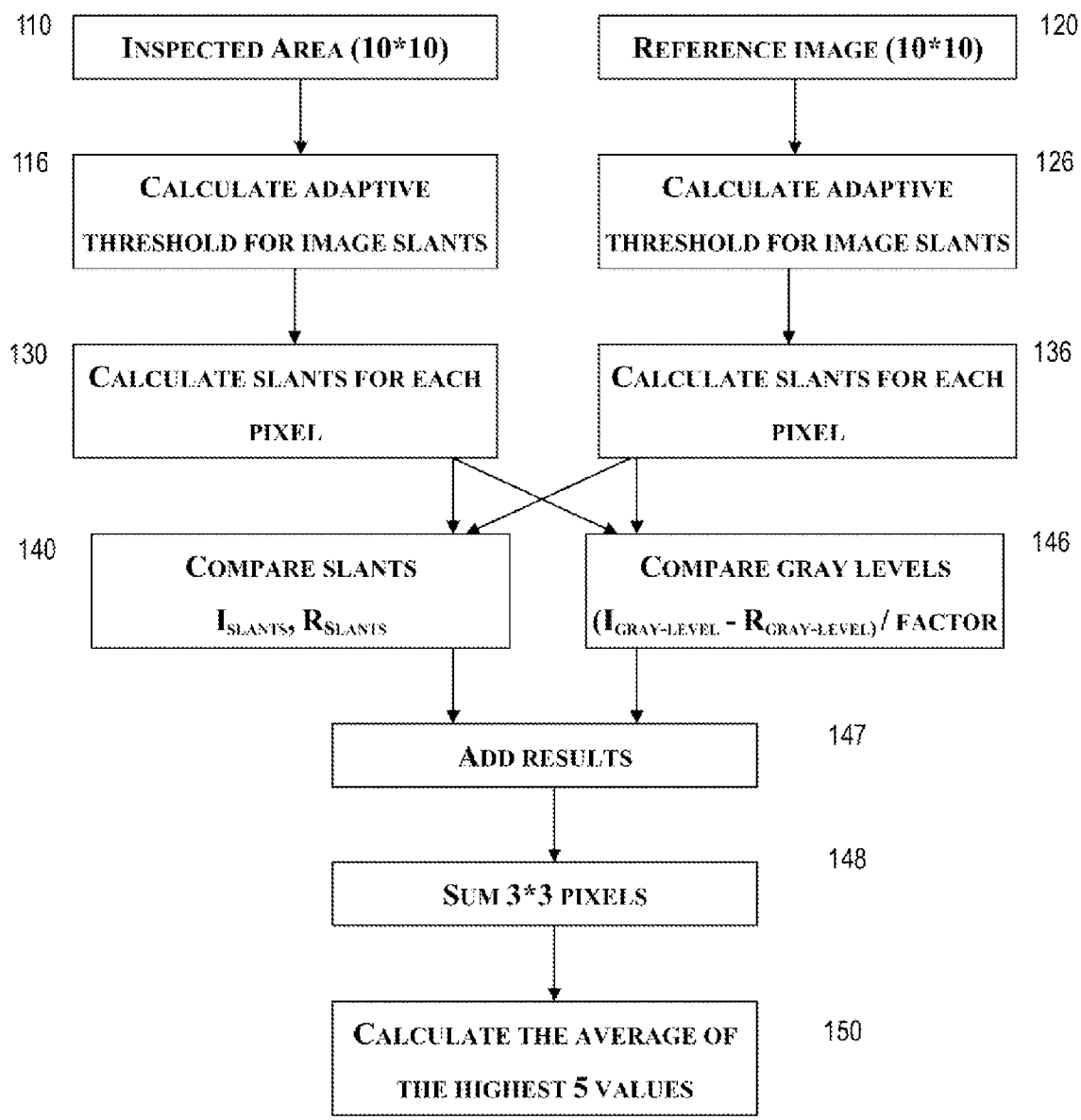
FIG. 5 is a flowchart showing exemplary steps in a method of defect detection.

An exemplary inspection process utilizing both conventional and relative-value-based analysis is depicted in FIG. 5. At steps 110 and 120, a 10×10 window from an inspection image and a reference image, respectively, are obtained using an optical inspection tool. For example, the window from the inspection image obtained at 110 may be an area indicated as containing a suspected defect. Alternatively, the window may be a sub-image of an inspection image that is being processed using a plurality of 10×10 windows in sequence.

At step 116, an adaptive threshold for the inspected image is calculated based on gray levels in the image, while at step 126 an adaptive threshold is calculated for the reference image based on gray levels therein. At step 130, directional vectors (i.e. slants) are calculated for each pixel in the 10×10 inspected window using the adaptive threshold. At step 136, directional vectors (i.e. slants) are calculated for each pixel in the 10×10 reference window using the reference window adaptive threshold.

At step 140, the slants for each pixel relative to each of its neighbors in the inspection image are compared to corresponding slants in the reference image to define a pixel slope correlation image. At step 146, the original inspection image and reference image are compared conventionally, for example, by subtraction. Furthermore, at step 146, the difference image (or other conventional output image) is divided by a factor.

At step 147, the pixel slope correlation image is added to the scaled difference image to obtain a total defect image. At step 148, a 3×3 sum operator is applied to the total defect image. At step 150, the area is flagged as containing a suspected defect if the average of the five highest values (after applying the sum operator) exceeds a given threshold.

One of skill in the art will appreciate that variations, substitutions, and other alterations of the steps discussed in conjunction with FIG. 5 are possible. For instance, ordinal values and a comparison metric may be used in addition to or instead of directional slopes. Furthermore, although a 10×10 window is discussed, larger, smaller, and/or differently-shaped windows may be utilized. Similarly, instead of a 3×3 sum operator, a sum operator of a different size or another type of spatial or other operator may be used. Although the conventional comparison that is discussed is a subtraction operation, other image comparison methods may be substituted. The output of the conventional comparison may be scaled and/or subjected to further processing before being combined with the output of the relative-value based comparison.

Figure 6:
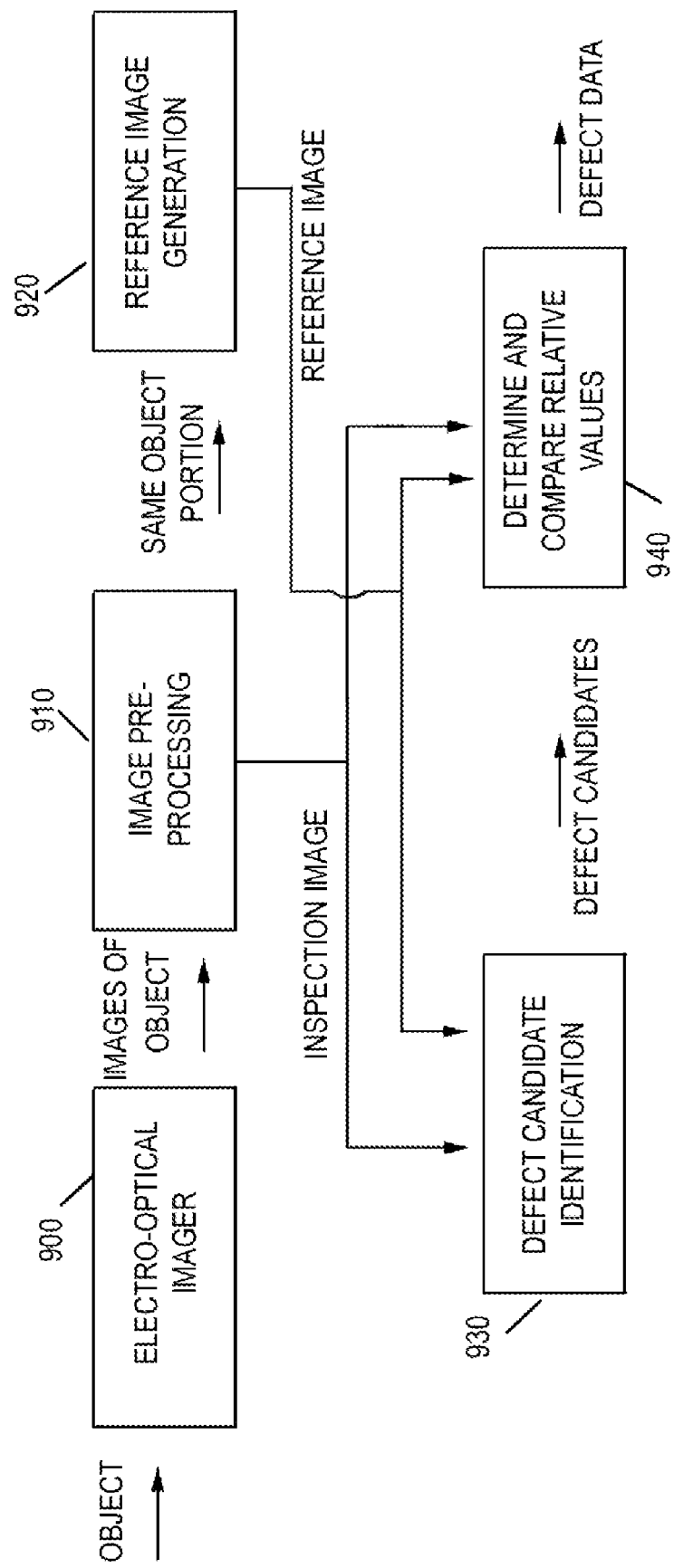
FIG. 6 is a block diagram showing the operation of an exemplary defect inspection system.

FIG. 6 is a block diagram illustrating a microscopic object inspection system constructed and operative in accordance with the subject matter discussed herein. Although illustrated as distinct blocks, the various illustrated components may be combined into or further divided into more or fewer physical or logical units than are illustrated in FIG. 6. Each of the illustrated components may be implemented using hardware and software components suitably configured and interfaced.

An electro-optical imager 900 such as that used in a Negevtech 302 wafer inspection tool, commercially available from Negevtech Ltd., 12 Hamada Street, Rehovot Israel 76703, generates a plurality of images of structural features of one or more objects to be inspected. For instance, the tool may operate in bright-field, dark-field, orthogonal dark field, or other modes and obtain images of several semiconductor wafers (or portions thereof).

The inspection system also includes image pre-processing unit 910. Pre-processing unit may include software and hardware configured to sort and align corresponding images of inspected objects. For example pre-processing unit 910 may be configured to align images of identical portions of inspected objects to one another. Other pre-processing operations may include adjusting or enhancing the brightness, contrast, or other properties of images. Image pre-processing unit may also be configured to divide images into portions for piecemeal detection and further operations.

Reference image generation unit 920 comprises hardware and software components configured to generate one or more reference images to be used in determining the presence or absence of defects. Reference image generation unit may, for example, obtain the median from a plurality of images provided by image pre-processing unit 910, with the images depicting the same structural features of an object. However, reference image generation unit may utilize other data sources in addition to or instead of other inspection images. For example, reference images may be derived from data including physical characteristics of the object being inspected.

A defect candidate identifier 930 is operative to compare an image to be inspected to a corresponding reference image. For example, the comparison may be made on a die-to-die or a cell-to-cell basis such as is described in U.S. patent application Ser. No. 11/069,712. In some embodiments, comparisons may be based on identifying the maximal differences in pixel intensities between the images. However, other modes of comparison and/or bases for comparison may be used. For example, as noted above, the reference image that is used may be derived from the combination of many images depicting ideally-identical structural features to those depicted in the inspection image. The defect candidate identification unit may perform a number of different operations before determining the existence of a possible defect.

One or more defect candidates may then be identified to a relative value based comparison unit 940. The identification may include data, for example, pixel coordinates, identifying where in the image the defect candidate occurs. The relative value based comparison unit 940 may then evaluate differences between the inspection and reference images based on ordinal values, directional vectors, and/or other relative measurements for an area of pixels surrounding the defect candidate(s).

For example, relative value based comparison unit may include logic and programming designed to assign ordinal values to pixels in the inspection and reference images and determine defects based on comparisons of ordinal ranks as discussed above. Alternatively, unit 940 may use one or more embodiments of the directional vector methods discussed above. Unit 940 may then provide defect data for further use in the inspection process. The defect data can include, for example, the relative value comparison results and the location of the defect candidate. For example, the defect data may be compared to a threshold, and if such threshold is met or exceeded, the defect may be flagged or otherwise noted for further analysis and processing.

One of ordinary skill in the art will appreciate that the methods described herein may be utilized with other types and arrangements of inspection and other tools. The various image processing steps and processes may be implemented using software, hardware, and combinations thereof. For example, certain steps may be implemented in programmable logic or other hardware in the inspection tool, with other steps implemented using software algorithms.

The various computer systems discussed herein are not limited to any particular hardware architecture or configuration. Any suitable programming, scripting, or other type of language or combinations of languages may be used to implement the teachings contained herein.

It is appreciated by persons skilled in the art that what has been particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed:

1. A method of electro-optically inspecting wafers, the method comprising:
    obtaining an inspection image of at least a part of a wafer using an optical inspection system;
    assigning a relative value to at least one pixel in the inspection image based on comparing the pixel to its neighboring pixels, wherein assigning the relative value includes at least one of (i) applying ordinal ranks to the at least one pixel and to its neighboring pixels in the inspection image and (ii) establishing a directional slope between the at least one pixel and its neighbors in the inspection image; and
    indicating a suspected defect in the inspection image based on comparing the at least one relative value of the inspection image to a relative value assigned to at least one pixel in a reference image, the reference image representing the same part of the wafer in the inspection image as it would appear in a substantially-defectless state.

2. The method as set forth in claim 1, further comprising filtering or smoothing the inspection image before assigning a relative value.

3. The method set forth in claim 1, further comprising:
    performing a gray level comparison between the inspection image and the reference image.

4. The method set forth in claim 1, wherein establishing a directional slope includes:
    selecting a characterization of a slope vector between two pixels in an image, the characterization selected from a group of more than three slope indicators.

5. The method set forth in claim 4, wherein the group of slope indicators includes at least one the following slope indicators: increasing, strongly increasing, decreasing, strongly decreasing, and undetermined.

6. The method set forth in claim 1, wherein assigning a relative value to at least one pixel includes:
    applying a jumping-window operator around the at least one pixel and one or more non-adjacent pixels.

7. The method as set forth in claim 1, wherein applying ordinal ranks to the at least one pixel and to its neighboring pixels in the inspection image includes:
    applying the ordinal ranks such that pixels with the same or close gray levels receive the same ordinal rank.

8. The method as set forth in claim 1, wherein the relative value assigned to the at least one pixel in the reference image is obtained from a pre-processed set of relative values.

9. An electro-optical inspection system comprising a light source configured to illuminate a wafer, an imager configured to obtain an image of the wafer, and a processing unit, wherein the processing unit is configured to:
    obtain an inspection image of at least a part of a wafer;
    assign a relative value to at least one pixel in the inspection image based on comparing the pixel to its neighboring pixels, wherein assigning the relative value includes at least one of (i) applying ordinal ranks to the at least one pixel and to its neighboring pixels in the inspection image and (ii) establishing a directional slope between the at least one pixel and its neighbors in the inspection image; and
    indicate a suspected defect in the inspection image based on comparing at least one relative value of the inspection image to a relative value assigned to at least one pixel in a reference image, the reference image representing the same part of the wafer in the inspection image as it would appear in a substantially defectless state.

10. The system set forth in claim 9, wherein the processing unit is further configured to filter or smooth the inspection image before assigning a relative value.

11. The system set forth in claim 9, wherein the processing unit is further configured to:
    perform a gray level comparison between the inspection image and the reference image.

12. The system set forth in claim 9, wherein establishing a directional slope includes:
    selecting a characterization of a slope vector between two pixels in an image, the characterization selected from a group of more than three slope indicators.

13. The system set forth in claim 12, wherein the group of slope indicators includes at least one the following slope indicators: increasing, strongly increasing, decreasing, strongly decreasing, and undetermined.

14. The system set forth in claim 9, wherein assigning a relative value to at least one pixel includes:
    applying a jumping-window operator around the at least one pixel and one or more non-adjacent pixels.

15. The system set forth in claim 9, wherein applying ordinal ranks to the at least one pixel and to its neighboring pixels in the inspection image.

16. The system as set forth in claim 9 wherein the processor is configured to obtain the relative value assigned to the at least one pixel in a reference image from a pre-processed set of relative values.

17. A method of detecting defects in an inspected object, the method comprising:
    a. obtaining an inspection image of at least a part of a wafer using an optical inspection system;
    b. obtaining a reference image, the reference image representing the same part of the wafer in the inspection image as it would appear in a substantially-defectless state;
    c. identifying at least one suspected defect in the inspection image;
    d. selecting at least one area in the inspection image containing the suspected defect and a corresponding area in the reference image for comparison;
    e. for each pixel in each area, establishing slope values for each pixel in each area relative to its surrounding pixels based on a threshold value;
    f. for each pixel in the area, comparing the amount of correlation between the established slope values for pixels in the inspection image and the established slope values for the corresponding pixels in the reference image, and determining, for each pixel, a pixel slope correlation value representing the amount of correlation;
    g. for each pixel in the area, comparing the gray levels of pixels in the inspection image to the corresponding gray levels of pixels in the reference image;
    h. for each pixel, determining a pixel defect value by adding the gray level comparison value to the pixel slope correlation value;
    i. applying a sum operator to the pixel defect values; and
    j. comparing at least some of the sum operator values to a threshold.

18. The method as set forth in claim 17, wherein comparing includes determining if the average of the five highest sum operator values in the area exceeds a threshold value.

19. An electro-optical inspection system comprising a light source configured to illuminate a wafer, an imager configured to obtain an image of the wafer, and a processing unit, wherein the processing unit is configured to:
  a. obtain an inspection image of at least a part of a wafer using an optical inspection system;
  b. obtain a reference image, the reference image representing the same part of the wafer in the inspection image as it would appear in a substantially-defectless state;
  c. identify at least one suspected defect in the inspection image;
  d. select at least one area in the inspection image containing the suspected defect and a corresponding area in the reference image for comparison;
  e. for each pixel in each area, establish slope values for each pixel in each area relative to its surrounding pixels based on a threshold value;
  f. for each pixel in the area, compare the amount of correlation between the established slope values for pixels in the inspection image and the established slope values for the corresponding pixels in the reference image, and determining, for each pixel, a pixel slope correlation value representing the amount of correlation;
  g. for each pixel in the area, compare the gray levels of pixels in the inspection image to the corresponding gray levels of pixels in the reference image and dividing the result by a factor to obtain a gray level comparison value for each pixel;
  h. for each pixel, determine a pixel defect value by adding the gray level comparison value to the pixel slope correlation value;
  i. apply a sum operator to the pixel defect values; and
  j. compare at least some of the sum operator values to a threshold.

20. The system set forth in claim 19, wherein comparing includes determining if the average of the five highest sum operator values in the area exceeds a threshold value.

* * * * *